United States Patent [19]
Edwards et al.

[11] Patent Number: 6,093,826
[45] Date of Patent: Jul. 25, 2000

[54] PROCESS FOR THE PREPARATION OF C(5)-SUBSTITUTED 1,2-DIHYDRO-5H-CHROMENO[3,4-F] QUINOLINES

[75] Inventors: James P. Edwards, San Diego; Todd K. Jones, Solana Beach, both of Calif.

[73] Assignee: Ligand Pharmaceuticals Incorporated, San Diego, Calif.

[21] Appl. No.: 09/093,421

[22] Filed: Jun. 8, 1998

[51] Int. Cl.[7] .................................................. C07D 471/00
[52] U.S. Cl. ................................................ 546/62; 546/13
[58] Field of Search .......................................... 546/13, 62

[56] References Cited

U.S. PATENT DOCUMENTS 5,696,127  12/1997  Jones et al. .

FOREIGN PATENT DOCUMENTS 9619458  6/1996  WIPO .

OTHER PUBLICATIONS

J.P. Edwards, S.J. West, K. B. Marschke, D. E. Mais, M. M. Gottardis, T. K. Jones, *J. Med. Chem.*, 41 (1998) 303–310.
T. M. Willson, J. Amburgey, S. E. Denmark, *J. Chem. Soc., Perkin Trans.*, 1 (1991) 2899–2906.
H. Fujioka, H. Kitagawa, Y. Nagatomi, Y. Kita, *J. Org. Chem.*, 61 (1996) 7309–7315.
T.–M. Yuan, S.–M. Yeh, Y.–T. Hsieh, T.–Y. Luh, *J. Org. Chem.*, 59 (1994) 8192–8196.
T. A. Grese, L. D. Pennington, *Tetrahedron Lett.*, 36 (1995) 8913–8916.

*Primary Examiner*—Alan L. Rotman
*Attorney, Agent, or Firm*—J. Scott Elmer; William L. Respess

[57] ABSTRACT

A method for preparing C(5)-substituted 1,2-dihydro-5H-chromeno[3,4-*f*]quinolines from a lactol precursor is provided. The method comprises converting the lactol to one of a select number of mixed acetal derivatives, and then treating the acetals with a Grignard reagent. The new process provides products in higher yield and greater purity. Novel intermediates of this method are also claimed.

1 Claim, No Drawings

PROCESS FOR THE PREPARATION OF C(5)-SUBSTITUTED 1,2-DIHYDRO-5H-CHROMENO[3,4-F] QUINOLINES

FIELD OF THE INVENTION

This invention relates to a process for the preparation of C(5)-substituted 1,2-dihydro-5H-chromeno[3,4-$f$]quinoline compounds that are useful as steroid receptor modulators.

BACKGROUND OF THE INVENTION

The 1,2-dihydro-5H-chromeno[3,4-$f$]quinolines of structure 3 are modulators of steroid receptor function. In particular, progesterone receptor (PR) and glucocorticoid receptor (GR) agonist and antagonist activity and androgen receptor (AR) antagonist activity have been noted for compounds in this class. {See: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, L. Zhi, J. P. Edwards, C. M. Tegley, S. J. West, U.S. Pat. No. 5,696,127; "5-Aryl-1,2-dihydro-5H-chromeno[3,4-$f$]quinolines as Potent, Orally Active, Nonsteroidal Progesterone Receptor Agonists: The Effect of D-Ring Substituents", J. P. Edwards, S. J. West, K. B. Marschke, D. E. Mais, M. M. Gottardis, T. K. Jones, *J. Med. Chem.* 41 (1998) 303–310.} Chromenoquinolines of structure 3 are prepared by a multi-step route culminating in the addition of an organometallic reagent to a lactone of structure 1 followed by reduction of the hemiketal intermediate 2 (R groups are defined under Detailed Description of the Invention):

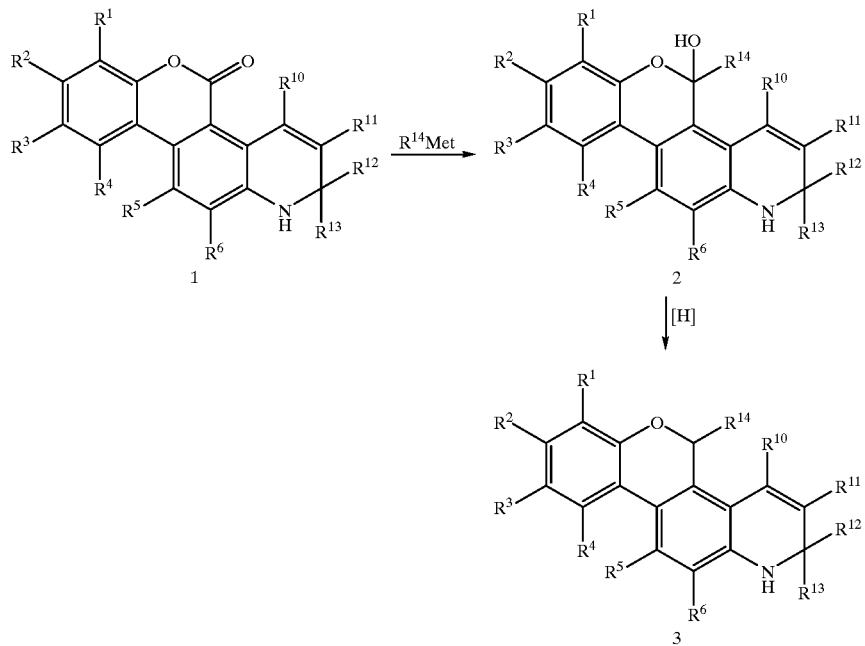

Alternatively, certain chromenoquinolines of structure 3 can be prepared in three steps from lactones 1 via acetals 5 by a Lewis-acid mediated nucleophilic substitution reaction using electron-rich olefins or electron-rich aromatic compounds as nucleophiles:

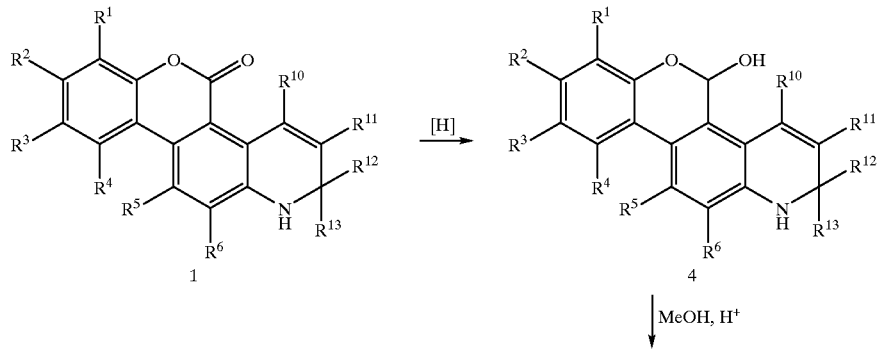

-continued

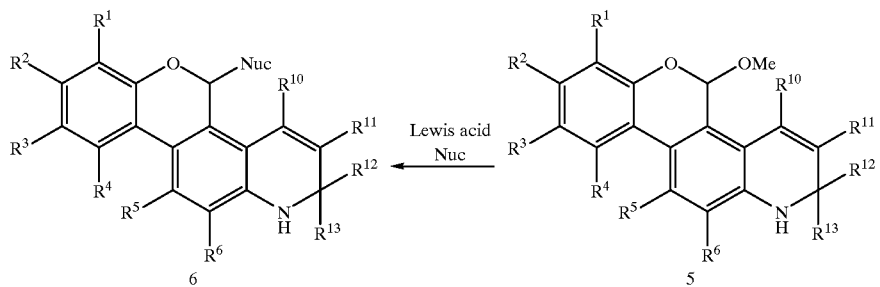

However, these two routes have drawbacks. In the first, the acidic medium required for reduction of hemiketals 2 ($R^{10}$=methyl or ethyl) often promotes the formation of undesired by-products of structure 7:

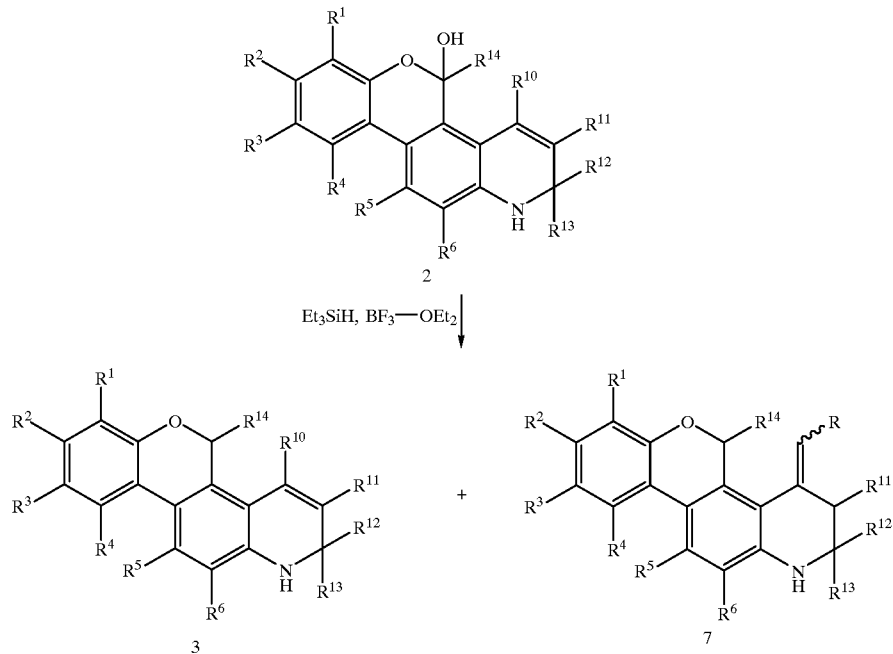

Additionally, only organolithium reagents add to lactone 1 with generality; for example, many alkyl magnesium halides afford complex mixtures when added to 1. And although certain aryllithium reagents add to the lactone functionality, the resulting hemiketal intermediate 2 cannot be reduced. The versatility of the second route is limited because the third step requires certain electron-rich nucleophiles.

SUMMARY OF THE INVENTION

The present invention provides a novel alternative for the conversion of lactols (hemiacetals) 4 to chromenoquinolines 3 by converting a lactol to one of a select number of mixed acetal derivatives of structure 8 or 9. The acetals 8 or 9 are then treated with an organomagnesium halide (Grignard reagent), thereby displacing the alcohol (or phenol) moiety introduced in the previous step:

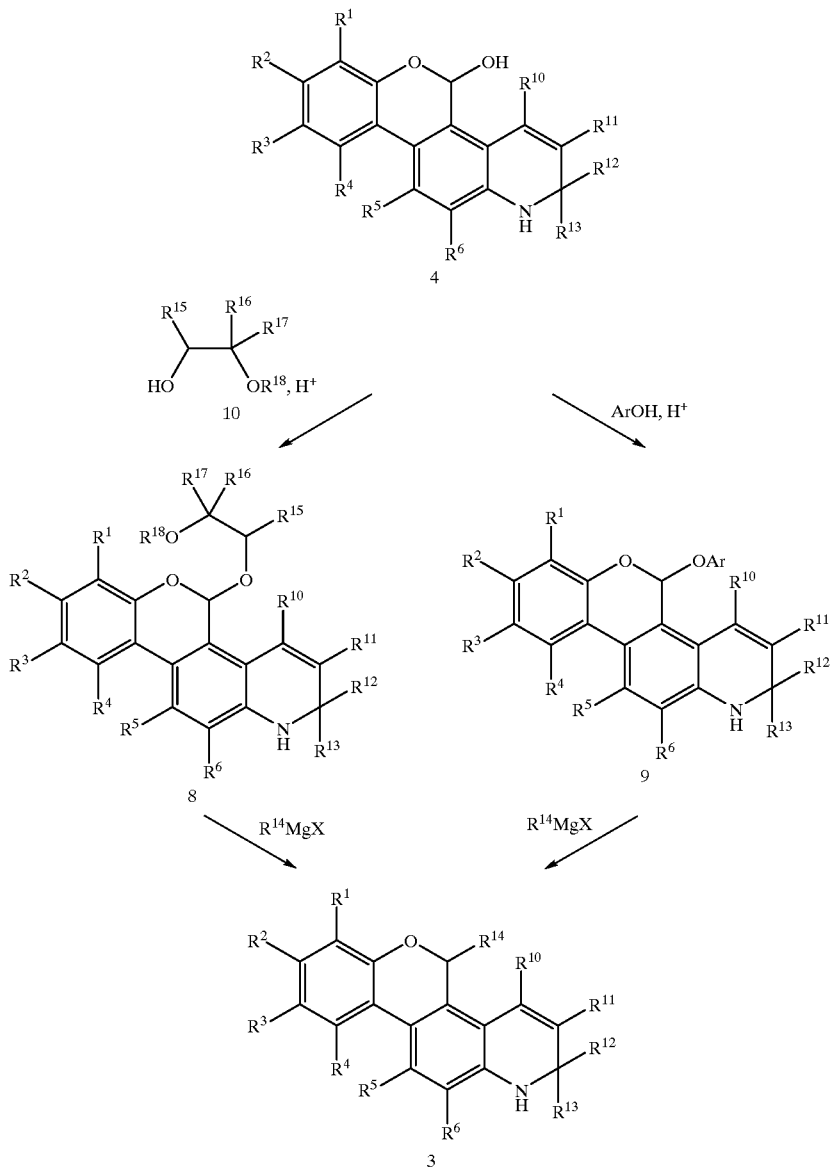

Related reactions of acetals or ketals with Grignard reagents have been previously reported. {See, for example: "Synthesis of α- and β-Branched Ethers from Alcohols by Reaction of Acetals with Grignard Reagents: Synthesis of Isopropyl and Isobutyl Ethers of (1S*,2R*S*,4R*)-6-Methylenebicyclo[2.2.2]octan-2-ol", T. M. Willson, J. Amburgey, S. E. Denmark, *J. Chem. Soc., Perkin Trans. 1* (1991) 2899; "Asymmetric Induction via an Intramolecular Haloetherification Reaction of Chiral Ene Acetals: A Novel Approach to Optically Active 1,4- and 1,5-Diols", H. Fujioka, H. Kitagawa, Y. Nagatomi, Y. Kita, *J. Org. Chem.* 61 (1996) 7309–7315; "Highly Diastereoselective Ring-Opening Reactions of Chiral Acetals with Secondary of Sterically Hindered Grignard Reagents", T. -M. Yuan, S. -M Yeh, Y. -T. Hsieh, T. -Y. Luh, *J. Org. Chem.* 59 (1994) 8192–8196; "Novel Methodology for the Synthesis of Estrogenic and Antiestrogenic 3-Isoflavenes", T. A. Grese, L. D. Pennington, *Tetrahedron Lett.* 36 (1995) 8913–16.} However reaction at a benzylic carbon in a ring has not been reported previously. Using this novel alternative procedure, chromenoquinolines of structure 3 are obtained in higher yields and require less purification. In addition, certain chromenoquinolines 3 that were difficult to access via the previous routes are now simple to obtain.

DETAILED DESCRIPTION OF THE INVENTION

In accordance with the present invention and as used herein, the following terms are defined with the following meanings, unless explicitly stated otherwise.

The terms "alkyl" and "allyl" refer to straight-chain, branched-chain, and cyclic structures, and combinations thereof. These "alkyl" and "allyl" structures may be optionally substituted with one or more heteroatoms, including for example, without limitation, fluorine, oxygen, nitrogen, phosphorus and sulfur.

The term "aryl" refers to an optionally substituted, six-membered aromatic ring, including polyaromatic rings.

The term "heteroaryl" refers to an optionally substituted, five-membered heterocyclic ring containing one or more heteroatoms selected from the group consisting of carbon, oxygen, nitrogen and sulfur, including polycyclic rings or six-membered heterocyclic rings containing one or more heteroatoms selected from the group consisting of carbon and nitrogen, including polycyclic rings.

In accordance with the present invention and as used herein, the following structure is provided for nomenclature purposes. In an effort to maintain consistency in the naming of compounds of similar structure but differing substituents, the compounds described herein are named according to the following general guidelines. Furthermore, the structure below is provided as a guide for the numbering system for location of substituents and may be optionally substituted, including with aryl and heteroaryl rings.

A 1,2-dihydro-5H-chromeno[3,4-$f$]quinoline is defined by the following structure:

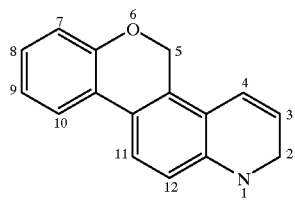

The novel process of the present invention begins with lactols (hemiacetals) 4 derived from the previously disclosed reduction of lactones 1 by a hydride delivery reagent {see: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, L. Zhi, J. P. Edwards, C. M. Tegley, S. J. West, U.S. Pat. No. 5,696,127}:

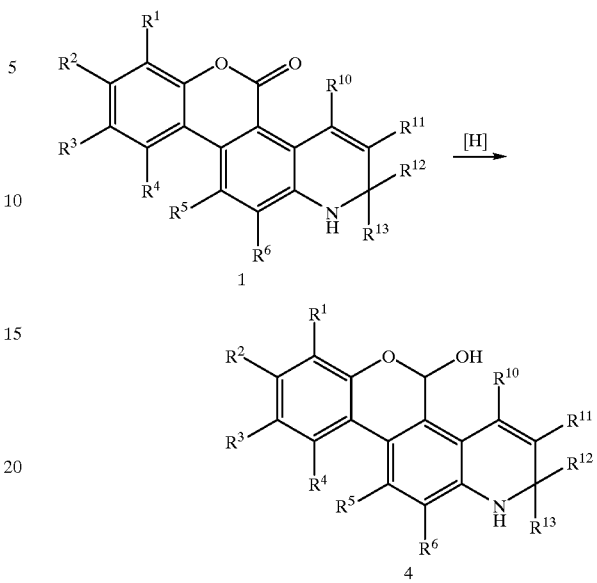

In the first step of the present invention, lactol 4 is converted to a mixed acetal derivative derived from either an optionally substituted 1,2-diol or 1,2-diol monoether 10 or an optionally substituted phenol (ArOH) by admixture of the ethanol or phenol with 4 in the presence of a catalyst, especially a Lewis acid or a protic acid such as para-toluenesulfonic acid or oxalic acid, in an inert solvent such as methylene chloride, benzotrifluride, 1,2-dichloroethane or toluene, to form either 8 or 9:

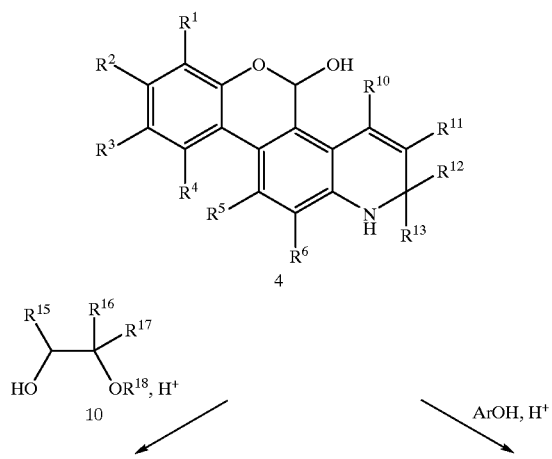

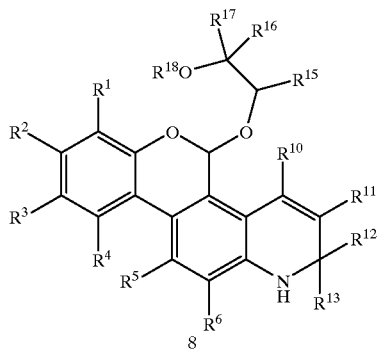
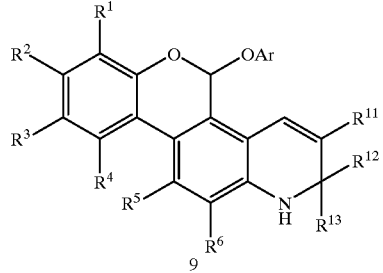

wherein $R^{1-6}$ independently represent H, $C_1$–$C_6$ alkyl, substituted $C_1$–$C_6$ alkyl, F, Cl, Cr, I, CN, $CF_3$, $CF_2CF_3$, $CO_2R^7$ (where $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered, optionally substituted ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, $SO_2R^9$;

$R^{10-11}$ independently represent H, $C_1$–$C_6$ alkyl, substituted $C_1$–$C_6$ alkyl, allyl, substituted allyl, aryl, substituted aryl, heteroaryl, substituted heteroaryl, $OR^9$ or Cl; $R^{12-13}$ independently represent $C_1$–$C_6$ alkyl, substituted $C_1$–$C_6$ alkyl, allyl, substituted allyl, aryl, substituted aryl, heteroaryl or substituted heteroaryl; or, alternatively, any two of $R^{10-13}$ can combine to form a three- to eight-membered (preferably four- to eight-membered), optionally substituted ring;

$R^{15-17}$ independently represent H, $C_1$–$C_6$ alkyl, substituted $C_1$–$C_6$ alkyl, allyl, substituted allyl, aryl, substituted aryl, heteroaryl or substituted heteroaryl; $R^{18}$ represents H, $C_1$–$C_6$ alkyl, benzyl or substituted benzyl; or, alternatively, any two of $R^{15}$–$R^{18}$ may combine to form a four- to seven-membered, optionally substituted ring; and the aryl group (Ar) on the C5 oxygen is optionally substituted.

In the final step, either mixed acetal derivative 8 or 9 is treated with an organomagnesium halide (Grignard reagent) in an inert solvent, especially diethyl ether, t-butyl methyl ether, toluene or methylene chloride, displacing the alkoxy (or aryloxy) group and affording the chromenoquinoline 3. The addition reaction can also be mediated by the presence of Lewis acid additives, especially zinc(II) chloride, cerium (III) chloride, chlorotitanium tri(isopropoxide), or titanium tetra(isopropoxide):

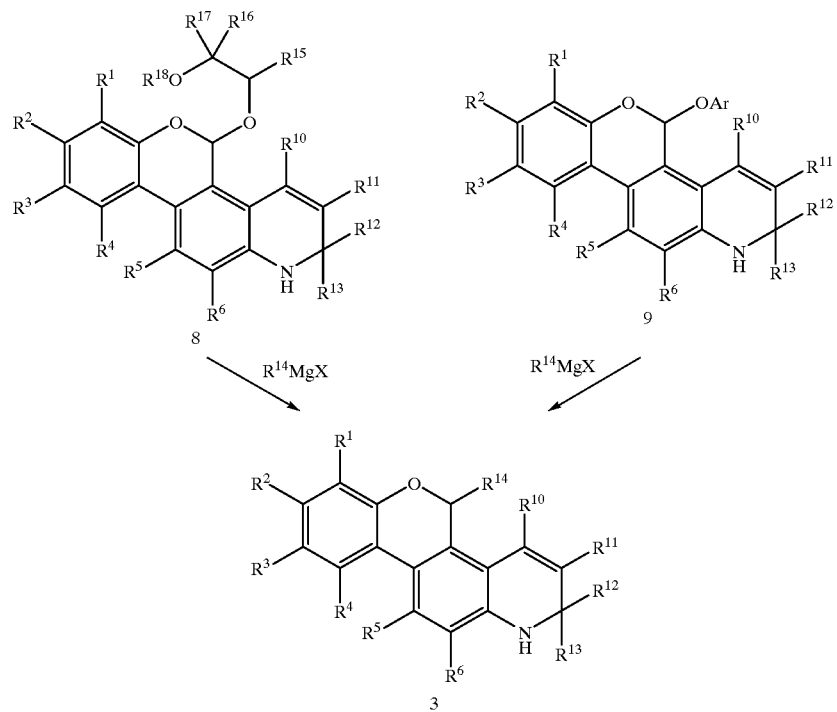

wherein $R^{14}$ is a $C_1$–$C_{12}$ alkyl, substituted $C_1$–$C_{12}$ alkyl, aryl, substituted aryl, heteroaryl, substituted heteroaryl, benzyl, substituted benzyl, allyl, substituted allyl, olefin, substituted olefin, alkyne or substituted alkyne.

The novel process of the present invention provides 1,2-dihydro-5H-chromeno[3,4-f]quinolines 3 in higher yields and requiring less purification than provided by previous routes. In addition, certain chromenoquinolines 3 that had been difficult to access are now simple to obtain. Chromenoquinolines 3 are modulators of steroid receptor function, and of PR, GR and AR activity in particular. {See: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K. Jones, L. Zhi, J. P. Edwards, C. M. Tegley, S. J. West, U.S. Pat. No. 5,696,127; "5-Aryl-1,2-dihydro-5H-chromeno[3,4-f]quinolines as Potent, Orally Active, Nonsteroidal Progesterone Receptor Agonists: The Effect of D-Ring Substituents", J. P. Edwards, S. J. West, K. B. Marschke, D. E. Mais, M. M. Gottardis, T. K. Jones, *J. Med. Chem.* 41 (1998) 303–310.}

The present invention also provides novel intermediates useful in the preparation of the steroid receptor modulator compounds of structure 3. The claimed intermediates of the present invention are defined as those having the structural formulas:

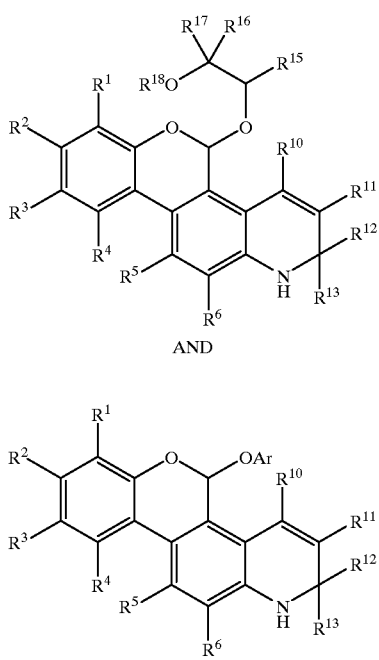

wherein $R^{1-6}$ independently represent H, $C_1$–$C_6$ alkyl, substituted $C_1$–$C_6$ alkyl, F, Cl, Br, I, CN, $CF_3$, $CF_2CF_3$, $CO_2R^7$ (wherein $R^7$ represents H, $C_1$–$C_6$ alkyl, substituted $C_1$–$C_6$ alkyl, allyl, substituted allyl, aryl, substituted aryl, heteroaryl or substituted heteroaryl), $CONR^7R^8$ (where $R^8$ represents H, $C_1$–$C_6$ alkyl, substituted $C_1$–$C_6$ alkyl, allyl, substituted allyl, aryl, substituted aryl, heteroaryl or substituted heteroaryl; or where, alternatively, $R^7$ and $R^8$ combine to form a four- to seven-membered, optionally substituted ring), $OR^9$ (where $R^9$ represents $C_1$–$C_6$ alkyl, substituted $C_1$–$C_6$ alkyl, allyl, substituted allyl, aryl, substituted aryl, heteroaryl or substituted heteroaryl), $NR^7R^9$, $SR^9$, $SOR^9$, $SO_2R^9$;

$R^{10-11}$ independently represent H, $C_1$–$C_6$ alkyl, substituted $C_1$–$C_6$ alkyl, allyl, substituted allyl, aryl, substituted aryl, heteroaryl, substituted heteroaryl, $OR^9$ or Cl; $R^{12-13}$ independently represent $C_1$–$C_6$ alkyl, substituted $C_1$–$C_6$ alkyl, allyl, substituted allyl, aryl, substituted aryl, heteroaryl or substituted heteroaryl; or, alternatively, any two of $R^{10-13}$ can combine to form a three- to eight-membered (preferably four- to eight-membered), optionally substituted ring;

$R^{15-17}$ independently represent H, $C_1$–$C_6$ alkyl, substituted $C_1$–$C_6$ alkyl, allyl, substituted allyl, aryl, substituted aryl, heteroaryl, substituted heteroaryl; and $R^{18}$ represents H, $C_1$–$C_6$ alkyl, benzyl or substituted benzyl; or, alternatively, any two of $R^{15-18}$ may combine to form a four- to seven-membered, optionally substituted ring; and the aryl group (Ar) on the C5 oxygen is optionally substituted.

All cited publications are incorporated by reference herein. All the processes and compounds disclosed in the cited publications are incorporated by reference herein, including those processes and compounds disclosed and referred to in articles cited by the publications mentioned herein.

EXAMPLE 1

Preparation of Structure 4 Lactol
9-Fluoro-1,2-dihydro-5-hydroxy-2,2,4-trimethyl-5H-chromeno[3,4-f]quinoline (compound 11; structure 4 where $R^{1-2}=R^{4-6}=R^{11}=H$; $R^3$=fluoro; $R^{10}=R^{12-13}$=methyl).

In a 250 mL 3-neck flask, a solution of lactone 12 (structure 1 where $R^{1-2}=R^{4-6}=R^{11}=H$; $R^3$=fluoro; $R^{10}=R^{12-13}$=methyl) (2.0 g, 6.5 mmol) in $CH_2Cl_2$ (150 mL) was cooled to −25° C. A 1.5 M solution of di(isobutyl)aluminum hydride in toluene (6.5 mL, 9.8 mmol, 1.5 equiv) was added via syringe over a 10-min period. The reaction mixture was stirred 5 min and an additional portion of 1.5 M di(isobutyl) aluminum hydride in toluene (2.0 mL, 3.0 mmol, 0.46 equiv) was added via syringe over a 5-min period. The reaction mixture was stirred for an additional 5 min and quenched by slow addition of 2.5% HCl (aq) (50 mL). The reaction mixture was allowed to warm to room temperature and stirred under an atmosphere of nitrogen for 1 h. The reaction mixture was poured into EtOAc (400 mL), and the layers were separated. The organic layer was washed with 5% HCl (aq) (2×100 mL), $H_2O$ (2×100 mL), saturated $NaHCO_3$ (1×100 mL), and brine (1×100 mL). The organic layer was dried ($Na_2SO_4$), filtered through a pad of Celite, and concentrated to a pale yellow solid. Purification by silica gel chromatography (hexane/$CH_2Cl_2$EtOAc, 5:4:1) afforded 1.81 g (90%) of 11 as an off-white solid. Data for 11: $^1H$ NMR (400 MHz, $CHCl_3$): 7.43 (d, J=8.3, 1H), 7.38 (dd, J=9.9, 3.0, 1H), 7.02 (dd, J=8.7, 4.9, 1H), 6.92 (m, 1H), 6.85 (d, J=7.4, 1H), 6.68 (d, J=8.3, 1H), 5.52 (s, 1H), 5.54 (d, J=1.4, 1H), 4.01 (exch s, 1H), 2.94 (d, J=7.3, 1H), 2.36 (s, 3H), 1.33 (s, 3H), 1.21 (s, 3H).

Step A
9-Fluoro-1,2-dihydro-2,2,4-trimethyl-5-phenoxy-5H-chromeno[3,4-f]quinoline (compound 13; structure 9 where $R^{1-2}=R^{4-6}=R^{11}=H$; $R^3$=fluoro; $R^{10}=R^{12-13}$=methyl; Ar=phenyl).

In a 100 mL r.b. flask, a solution of 11 (405 mg, 1.30 mmol) in $CH_2Cl_2$ (15 mL) was treated with phenol (160 mg, 1.70 mmol, 1.31 equiv), 4 Å sieves (0.1 g), and para-toluenesulfonic acid hydrate (10 mg). The reaction mixture was stirred for 12 h at room temperature, poured into saturated $NaHCO_3$ (40 mL), and extracted with EtOAc (3×40 mL). The extracts were washed with brine (1×40 mL), combined, dried (K$_2$CO$_3$), filtered, and concentrated. Purification by silica gel chromatography (hexane/EtOAc, 8.1) afforded 0.45 g (88%) of 13 as a pale yellow solid. Data for 13: $^1$H NMR (400 MHz, acetone-d$_6$): 7.64 (d, J=8.6, 1H), 7.56 (dd, J=10.0, 2.8, 1H), 7.34 (m, 3H), 7.21 (d, J=8.0, 1H), 7.19 (d, J=8.6, 1H), 7.03 (t, J=7.3, 1H), 6.86 (m, 3H), 5.72 (exch s, 1H), 5.52 (s, 1H), 2.10 (d, J=2.0, 3H), 1.33 (s, 3H), 1.19 (s, 3H).

Step B
9-Fluoro-1,2-dihydro-2,2,4-trimethyl-5-phenyl-5H-chromeno[3,4-*f*]quinoline (compound 14; structure 3 where R$^{1-2}$=R$^{4-6}$=R$^{11}$=H; R$^3$=fluoro; R$^{10}$=R$^{12-13}$=methyl; R$^{14}$=phenyl).

In a 10 mL r.b. flask, a solution of 13 (101 mg, 0.26 mmol) in Et$_2$O (1.0 mL) was treated with a 3.0 M solution of phenylmagnesium bromide in Et$_2$O (0.26 mL, 3.0 equiv). The reaction mixture was stirred at room temperature for 15 min and quenched by the addition of saturated NH$_4$Cl (2 mL). The reaction mixture was poured into H$_2$O (4 mL) and extracted with EtOAc (3×5 mL). The extracts were washed with brine (1×5 mL), combined, dried (MgSO$_4$), filtered, and concentrated. Purification by silica gel chromatography (hexane/EtOAc, 8:1) afforded 65 mg (67%) of 14 as a white solid. Data for 14: $^1$H NMR (400 MHz, benzene-d$_6$): 7.30 (d, J=7.6, 1H), 7.23 (dd, J=9.6, 3.0, 1H), 7.17 (d, J=8.3, 1H), 6.99 (s, 1H), 6.95 (t, J=7.6, 2H), 6.86 (t, J=7.6, 1H), 6.73 (dd, J=8.6, 4.9, 1H), 6.50 (td, J=8.6, 3.0, 1H), 6.24 (d, J=8.3, 1H), 5.10 (s, 1 H), 3.40 (br s, 1H), 1.77 (d, J=1.2, 3 H), 0.99 (s, 3 H), 0.98 (s, 3 H); $^{13}$C NMR (400 MHz, benzene-d$_6$): 159.1 (d, J$_{C-F}$=237), 147.8, 146.3, 140.5, 133.7, 130.9, 129.4, 129.1, 128.7, 128.5, 126.9 (d, J$_{C-F}$=8.0), 124.7, 121.2, 120.0, 119.3 (d, J$_{C-F}$=8.6), 115.5, 114.4 (d, J$_{C-F}$=23), 109.1 (d, J$_{C-F}$=25), 76.6, 50.9, 39.2, 24.2.

EXAMPLE 2

Step A
9-Fluoro-1,2-dihydro-5-(2-methoxyethoxy)-2,2,4-trimethyl-5H-chromeno[3,4-*f*]quinoline (compound 15; structure 8 where R$^{1-2}$=R$^{4-6}$=R$^{11}$=R$^{15-17}$=H; R$^3$=fluoro; R$^{10}$=R$^{12-13}$=R$^{18}$=methyl).

In a 20 mL r.b. flask, a suspension of 11 (135 mg, 0.434 mmol) in toluene (2 mL) was treated with 2-methoxyethanol (0.10 mL, 1.3 mmol, 2.9 equiv), para-toluenesulfonic acid hydrate (3 mg), and 4 Å sieves (8). The reaction mixture was warmed to 60° C. for 4 h, allowed to cool to room temperature, poured into saturated NaHCO$_3$ (8 mL), and extracted with EtOAc (3×10 mL). The extracts were washed with brine (1×10 mL), combined, dried (K$_2$CO$_3$), filtered, and concentrated to a yellow solid. Purification by silica gel chromatography (hexane/EtOAc, 4:1) afforded 147 mg (92%) of 15 as an off-white solid. Data for 15: $^1$H NMR (400 MHz, benzene-d$_6$): 7.34 (dd, J=9.7, 3.0, 1H), 7.11 (d, J=8.4, 1H), 6.92 (dd, J=8.7, 4.9, 1H), 6.75 (m, 1H), 6.49 (s, 1H), 6.16 (d, J=8.2, 1H), 5.22 (s, 1H), 3.87 (dt, J=10.5, 4.2, 1H), 3.64 (m, 1H), 3.32 (exch s, 1H), 3.18 (m, 1H), 3.13 (m, 1H), 2.91 (s, 3H), 2.19 (d, J=1.1, 3H), 0.99 (s, 3H), 0.94 (s, 3H); $^{13}$C NMR (100 MHz, CHCl$_3$): 158.7 (d, J$_{C-F}$=238), 145.6, 144.4, 133.3, 128.8, 127.8, 125.2 (d, J$_{C-F}$=7.7), 123.8, 119.2, 118.4 (d, J$_{C-F}$=8.6), 116.0, 113.7 (d, J$_{C-F}$=24), 108.8 (d, J$_{C-F}$=25), 96.3, 71.5, 67.4, 59.1, 50.8, 30.5, 28.6, 23.0.

Step B
9-Fluoro-1,2-dihydro-2,2,4-trimethyl-5-phenyl-5H-chromeno[3,4-*f*]quinoline (compound 14; structure 3 where R$^{1-2}$=R$^{4-6}$=R$^{11}$=H; R$^3$=fluoro; R$^{10}$=R$^{12-13}$=methyl; R$^{14}$=phenyl).

In a 20 mL r.b. flask, to a solution of 15 (27 mg, 0.073 mmol) in toluene (1 mL) was added a 3.0 M solution of PhMgBr in Et$_2$O (0.10 mL, 0.30 mmol, 4.0 equiv). The reaction mixture was stirred for 10 min, poured into saturated NH$_4$Cl (5 mL), and extracted with EtOAc (3×4 mL). The extracts were washed with brine (1×5 mL), combined, dried (MgSO$_4$), filtered, and concentrated. Purification by silica gel chromatography (hexane/CH$_2$Cl$_2$, 1:1) afforded 20 mg (77%) of compound 14, identical to samples prepared previously.

EXAMPLE 3

Step A
9-Fluoro-1,2-dihydro-5-(4-methoxyphenoxy)-2,2,4-trimethyl-5H-chromeno[3,4-*f*]quinoline (compound 16; structure 9 where R$^{1-2}$=R$^{4-6}$=R$^{11}$=H; R$^3$=fluoro; R$^{10}$=R$^{12-13}$=methyl; Ar=4-methoxyphenyl).

In a 100 mL r.b. flask, a solution of 11 (544 mg, 1.75 mmol) in CH$_2$Cl$_2$ (25 mL) was treated with 4-methoxyphenol (651 mg, 5.24 mmol, 3.0 equiv), 4 Å sieves (0.2 g), and para-toluenesulfonic acid hydrate (20 mg). The reaction mixture was stirred for 12 h at room temperature, poured into saturated NaHCO$_3$ (40 mL), and extracted with EtOAc (3×40 mL). The extracts were washed with brine (1×40 mL), combined, dried (K$_2$CO$_3$), filtered, and concentrated to a pale yellow oil. Purification by trituration with hexanes afforded 550 g (75%) of 16 as a pale yellow solid. Data for 16: $^1$H NMR (400 MHz, CDCl$_3$): 7.48 (d, J=8.4, 1H), 7.40 (dd, J=9.7, 2.5, 1H), 7.10 (m, 2H), 6.90 (m, 1H), 6.80 (m, 3H), 6.65 (m, 2H), 5.49 (s, 1H), 4.05 (br exch s, 1H), 3.78 (s, 3H), 2.11 (s, 3H), 1.33 (s, 3H), 1.19 (s, 3H); $^{13}$C NMR (100 MHz, acetone-d$_6$): 159.5 (d, J$_{C-F}$=236), 155.9, 151.2, 147.6, 145.0, 134.2, 134.1, 128.8, 127.5, 126.2 (d, J$_{C-F}$=8.4), 124.5, 119.2 (d, J$_{C-F}$=8.9), 118.7, 1181, 116.8, 115.5, 113.8 (d, J$_{C-F}$=24), 109.0 (d, J$_{C-F}$=25), 94.7, 55.7, 51.0, 28.5, 23.7.

Step B
9-Fluoro-1,2-dihydro-5-(3-methylphenyl)-2,2,4-trimethyl-5H-chromeno[3,4-*f*]quinoline (compound 17; structure 3 where R$^{1-2}$=R$^{4-6}$=R$^{11}$=H; R$^3$=fluoro; R$^{10}$=R$^{12-13}$=methyl; R$^{14}$=3-methylphenyl).

In a 25 mL r.b. flask, a solution of 16 (100 mg, 0.24 mmol)) in THF (1.0 mL) was treated with a 1.0 M solution of m-tolylmagnesium bromide in THF (0.72 mL, 0.72 mmol, 3.0 equiv). The reaction mixture was stirred at room temperature for 15 min and quenched by the addition of saturated NH$_4$Cl (2 mL). The reaction mixture was poured into H$_2$O (4 mL) and extracted with EtOAc (3×5 mL). The extracts were washed with brine (1×5 mL), combined, dried (MgSO$_4$), filtered, and concentrated. Purification by silica gel chromatography (hexane/EtOAc, 8:1) afforded 44 mg (48%) of 17 as a white solid. Data for 17: $^1$H NMR (400 MHz, benzene-d$_6$): 7.25 (dd, J=9.6, 2.9, 1H), 7.20 (d, J=10.0, 2H), 7.02 (s, 1H), 6.91 (t, J=7.6, 1H), 6.77 (m, 1H), 6.71 (d, J=7.6, 2H), 6.51 (td, J=8.4, 2.9, 1H), 6.25 (d, J=8.3, 1H), 5.11 (s, 1H), 3.39 (br s, 1H), 1.92 (s, 3H), 1.82 (s, 3H), 1.00 (s, 3H), 0.99 (s, 3H); $^{13}$C NMR (100 MHz, benzene-d$_6$): 159.1 (d, J$_{C-F}$=237), 147.9, 146.3, 140.6, 138.2, 133.7, 131.1, 129.8, 129.4, 128.7, 128.3, 126.9 (d, J$_{C-F}$=8.8), 126.4, 124.7, 121.3, 120.0, 119.3 (d, J$_{C-F}$=8.6), 115.5, 114.4 (d, J$_{C-F}$=24), 109.2 (d, J$_{C-F}$=24), 76.7, 50.9, 30.0, 29.1, 24.2, 21.6.

EXAMPLE 4
9-Fluoro-1,2-dihydro-2,2,4-trimethyl-5-phenyl-5H-chromeno[3,4-*f*]quinoline (compound 14; structure 3 where R$^{1-2}$=R$^{4-6}$=RR$^{11}$=H; R$^3$=fluoro; R$^{10}$=R$^{12-13}$=methyl; R$^{14}$=phenyl).

In a 20 mL r.b. flask, ZnCl$_2$ (7 mg) was suspended in Et$_2$O (3 mL) and treated with a 3.0 M solution of PhMgBr in Et$_2$O (0.24 mL, 0.72 mmol, 3.0 equiv). The reaction mixture was stirred at room temperature for 45 min. A portion of 16 (100 mg, 0.24 mmol) was added as a solid. The reaction mixture was stirred for 20 min, poured into saturated NH$_4$Cl (5 mL), and extracted with EtOAc (3×4 mL). The extracts were washed with brine (1×5 mL), combined, dried (MgSO$_4$), filtered, and concentrated. Purification by silica gel chromatography (hexane/EtOAc, 10:1) afforded 68 mg (76%) of compound 14, identical to samples prepared previously.

EXAMPLE 5

Step A

9-Fluoro-1,2-dihydro-5-(2-hydroxy-1-methyl-2,2-diphenylethoxy)-2,2,4-trimethyl-5H-chromeno[3,4-*f*] quinoline (compound 18; structure 8 where $R^{1-2}=R^{4-6}=R^{11}=R^{18}=H$; $R^3$=fluoro; $R^{10}=R^{12-13}=R^{15}$=methyl; $R^{16-17}$=phenyl).

In a 200 mL r.b. flask, to a solution of 11 (1.72 g, 5.52 mmol) in CH$_2$Cl$_2$ (40 mL) was added (S)-1,1-diphenyl-1,2-propanediol (2.28 g, 1.81 equiv), para-toluenesulfonic acid hydrate (121 mg, 0.64 mmol, 11 mol %), and 4 Å sieves (0.5 g). The reaction mixture was stirred at room temperature for 14 h, filtered, poured into saturated NaHCO$_3$ (50 mL), and extracted with EtOAc (3×60 mL). The extracts were washed with brine (1×50 mL), combined, dried (K$_2$CO$_3$), filtered, and concentrated. Purification by silica gel chromatography (hexane/EtOAc, 8:1) afforded 2.46 g (85%) of 18 as a white solid. The $^1$H NMR spectrum of this material indicated a >10:1 mixture of two diastereomers (data for major diastereomer only). Data for 18: $^1$H NMR (400 MHz, benzene-d$_6$): 7.40 (m, 3H), 7.10 (m, 6H), 6.95 (m, 3H), 6.80 (m, 2H), 6.73 (s, 1H), 6.07 (d, J=8.4, 1H), 5.16 (s, 1H), 4.96 (q, J=6.2, 1H), 3.30 (exch s, 1H), 2.44 (exch s, 1H), 2.00 (d, J=1.1, 3H), 1.28 (d, J=6.2, 3H), 0.99 (s, 3H), 0.91 (s, 3H).

Step B

9-Fluoro-1,2-dihydro-2,2,4-trimethyl-5-phenyl-5H-chromeno[3,4-*f*]quinoline (compound 14; structure 3 where $R^{1-2}=R^{4-6}=R^{11}$=H; $R^3$=fluoro; $R^{10}=R^{12-13}$=methyl; $R^{14}$=phenyl).

In a 25 mL 2-neck flask a 3.0 M solution of PhMgBr in Et$_2$O (0.22 mL, 0.66 mmol, 4.0 equiv) was diluted with Et$_2$O (1.0 mL) and cooled to 0° C. A 1.0 M solution of chlorotitanium tri(isopropoxide) in hexanes (0.68 mL, 0.68 mmol, 4.0 equiv) was added and the reaction mixture was stirred at 0° C. for 30 min. A solution of 18 (89 mg, 0.17 mmol) in Et$_2$O (1.0 mL) was added via syringe and the reaction mixture was allowed to warm to room temperature. The reaction mixture was stirred for 12 h, poured into saturated NH$_4$Cl (5 mL), and extracted with EtOAc (3×4 mL). The extracts were washed with brine (1×5 mL), combined, dried (MgSO$_4$), filtered, and concentrated. Purification by silica gel chromatography (hexane/EtOAc, 10:1) afforded 27 mg (48%) of compound 14, identical to samples prepared previously.

EXAMPLE 6

5-(3-Chlorophenyl)-9-fluoro-1,2-dihydro-2,2,4-trimethyl-5H-chromeno[3,4-*f*]quinoline (compound 19; structure 3 where $R^{1-2}=R^{4-6}=R^{11}$=H; $R^3$=fluoro; $R^{10}=R^{12-13}$=methyl; $R^{14}$=3-chlorophenyl).

In a 25 mL 2-neck flask a solution of 18 (85 mg, 0.16 mmol) in Et$_2$O (1.0 mL) was cooled to 0° C. and treated with a 2.5 M solution of n-butyllithium in hexanes (70 µL, 0.18 mmol, 1.0 equiv) and the reaction mixture was stirred for 15 min. A 1.0 M solution of chlorotitanium tri(isopropoxide) in hexanes (0.18 mL, 0.18 mmol, 1.0 equiv) was added and the reaction mixture was stirred at 0° C. for 15 min. A 1.0 M solution of m-chlorophenylmagnesium bromide in Et$_2$O (0.65 mL, 0.65 mmol, 4.0 equiv) was added and the reaction mixture was stirred for 20 min. The reaction mixture was poured into saturated NH$_2$Cl (5 mL), and extracted with EtOAc (3×4 mL). The extracts were washed with brine (1×5 mL), combined, dried (MgSO$_4$), filtered, and concentrated. Purification by silica gel chromatography (hexane/EtOAc, 10:1) afforded 39 mg (59%) of compound 19. Data for 19: $^1$H NMR (400 MHz, acetone-d$_6$): 7.55 (d, J=8.4, 1H), 7.35 (dd, J=9.9, 2.9, 1H), 7.20 (m, 4H), 6.93 (s, 1H), 6.84 (d, J=8.4, 1H), 6.81 (dd, J=8.5, 5.0, 1H), 6.73 (td, J=8.5, 2.9, 1H), 5.67 (br s, 1H), 5.49 (s, 1 H), 1.99 (s, 3 H), 1.27 (s, 3 H, 1.24 (s, 3 H); $^{13}$C NMR (100 MHz, acetone-d$_6$): 159.2 (d, J$_{C-F}$=236), 147.8, 143.5, 134.8, 134.6, 130.7, 129.9, 129.1, 128.9, 127.8, 127.1 (d, J$_{C-F}$=7.9), 125.0, 119.7, 119.6, 119.4 (d, J$_{C-F}$=9.0), 116.1, 114.2 (d, J$_{C-F}$=24), 109.1 (d, J$_{C-F}$=25), 75.7, 51.2, 29.7, 29.4, 24.1.

EXAMPLE 7

9-Fluoro-1,2-dihydro-5-isopropyl-2,2,4-trimethyl-5H-chromeno[3,4-*f*]quinoline (compound 20; structure 3 where $R^{1-2}=R^{4-6}=R^{11}$=H; $R^3$=fluoro; $R^{10}=R^{12-13}$=methyl; $R^{14}$=isopropyl).

In a 20 mL r.b. flask, to a solution of 15 (50 mg, 0.13 mmol) in Et$_2$O (1 mL) was added a 2.0 M solution of isopropylmagnesium bromide in THF (0.20 mL, 0.40 mmol, 3.1 equiv). The reaction mixture was stirred for 10 min, poured into saturated NH$_4$Cl (5 mL), and extracted with EtOAc (3×4 mL). The extracts were washed with brine (1×5 mL), combined, dried (MgSO$_4$), filtered, and concentrated. Purification by silica gel chromatography (hexane/EtOAc, 12:1) afforded 36 mg (84%) of compound 20 as a clear oil. Data for 20: $^1$H NMR (400 MHz, benzene-d$_6$): 7.37 (dd, J=9.8, 2.9, 1H), 7.13 (d, J=8.4, 1H), 6.83 (dd, J=8.8, 4.9, 1H), 6.72 (td, J=8.4, 2.9, 1H), 6.17 (d, J=8.4, 1H), 5.56 (d, J=9.3, 1H), 5.15 (d, J=0.9, 1H), 3.35 (br exch s, 1H), 2.03 (m, 1H), 1.97 (s, 3H); 1.04 (d, J=6.7, 3H), 1.03 (s, 3 H); 0.90 (s, 3 H), 0.68 (d, J=6.7, 3H); $^{13}$C NMR (100 MHz, acetone-d$_6$): 159.2 (d, J$_{C-F}$=236), 147.8, 143.5, 134.8, 134.6, 130.7, 129.9, 129.1, 128.9, 127.8, 127.1 (d, J$_{C-F}$=7.9), 125.0, 119.7, 119.6, 119.4 (d, J$_{C-F}$=9.0), 116.1, 114.2 (d, J$_{C-F}$=24), 109.1 (d, J$_{C-F}$=25), 75.7, 51.2, 29.7, 29.4, 24.1.

We claim:

1. A compound having structural formula 8

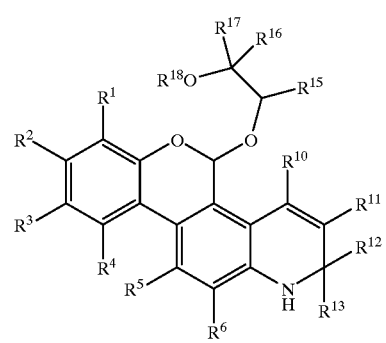

wherein $R^{1-1}$ independently represent H, C$_1$–C$_6$ alkyl, substituted C$_1$–C$_6$ alkyl, F, Cl, Br, I, CN, CF$_3$, CF$_2$CF$_3$, OR$^9$ (where R$^9$ represents H, C$_1$–C$_6$ alkyl, and substituted C$_1$–C$_6$ alkyl), NR'R$^9$, (where R$^7$ represents H and C$_1$–C$_6$ alkyl), SR$^9$, SOR$^9$, SO$_2$R$^9$;

$R^5$ and $R^6$ each represent H;

$R^{10}$ represents H, $C_1$–$C_6$ alkyl, substituted $C_1$–$C_6$ alkyl, $OR^9$ or Cl;

$R^{11}$ represents H;

$R^{12\text{-}13}$ independently represent $C_1$–$C_6$ alkyl, substituted $C_1$–$C_6$ alkyl;

$R^{16\text{-}17}$ independently represent H, $C_1$–$C_6$ alkyl, allyl, and aryl; and $R^{18}$ represents H, $C_1$–$C_6$ alkyl, benzyl; or, alternatively, any two of $R^{15\text{-}18}$ may combine to form a four- to seven-membered, optionally substituted ring.

* * * * *